(12) United States Patent
Stainsby et al.

(10) Patent No.: US 11,650,273 B2
(45) Date of Patent: *May 16, 2023

(54) ADAPTIVE SHIM COILS FOR MR IMAGING

(71) Applicant: SYNAPTIVE MEDICAL INC., Toronto (CA)

(72) Inventors: Jeff Alan Stainsby, Toronto (CA); Chad Tyler Harris, Toronto (CA)

(73) Assignee: Synaptive Medical Inc.

( * ) Notice: Subject to any disclaimer, the term of this patent is extended or adjusted under 35 U.S.C. 154(b) by 0 days.

This patent is subject to a terminal disclaimer.

(21) Appl. No.: 17/658,054

(22) Filed: Apr. 5, 2022

(65) Prior Publication Data

US 2022/0229131 A1 Jul. 21, 2022

Related U.S. Application Data

(63) Continuation of application No. 16/316,707, filed as application No. PCT/IB2016/054140 on Jul. 11, 2016, now Pat. No. 11,300,643.

(51) Int. Cl.
*G01R 33/3875* (2006.01)
*A61B 5/055* (2006.01)
*G01R 33/38* (2006.01)
*G01R 33/381* (2006.01)

(52) U.S. Cl.
CPC ......... *G01R 33/3875* (2013.01); *A61B 5/055* (2013.01); *G01R 33/3806* (2013.01); *G01R 33/381* (2013.01)

(58) Field of Classification Search
CPC ............ G01R 33/3875; G01R 33/3806; G01R 33/381; G01R 33/483; A61B 5/055
See application file for complete search history.

(56) References Cited

U.S. PATENT DOCUMENTS 11,300,643 B2 * 4/2022 Stainsby ............ G01R 33/3806
2014/0327440 A1 * 11/2014 Nakanishi .......... G01R 33/3875
324/309

OTHER PUBLICATIONS

Jeff Alan Stainsby et al., "Adaptive Shim Coils for MR Imaging", U.S. Appl. No. 16/316,707, filed Jan. 10, 2019, Notice of Allowance issued.

* cited by examiner

*Primary Examiner* — Rishi R Patel

(57) ABSTRACT

Systems and methods involving: a housing having a bore in which a subject to be imaged is placed; a main magnet configured to generate a volume of magnetic field within the bore, the volume of magnetic field having inhomogeneity below a defined threshold; gradient coils configured to linearly vary the volume of magnetic field as a function of spatial location; pulse-generating coils configured to generate and apply radio frequency (RF) pulses to the volume of magnetic field in sequence to scan the portion of the subject; shim gradient coils configured to perturb a spatial distribution of the linearly varying volume of magnetic field; and a control unit configured to operate the gradient coils, pulse-generating coils, and shim gradient coils such that only the user-defined region within the volume of magnetic field is imaged.

20 Claims, 6 Drawing Sheets

ADAPTIVE SHIM COILS FOR MR IMAGING

CROSS-REFERENCE TO RELATED APPLICATION(S)

This document is a continuation application claiming the benefit of, and priority to U.S. patent application Ser. No. 16/316,707, entitled "ADAPTIVE SHIM COILS FOR MR IMAGING," filed on Jan. 10, 2019, and International Patent Application No. PCT/IB2016/054140, entitled "ADAPTIVE SHIM COILS FOR MR IMAGING," filed on Jul. 11, 2016, all of which are hereby incorporated by reference herein in their entirety.

FIELD

The present disclosure relates to magnetic resonance imaging and thermal dissipation.

BACKGROUND

In the related art, magnetic resonance is used for imaging.

SUMMARY

In an implementation of the present disclosure, a magnetic resonance imaging (MRI) system comprises: a main magnet configured to generate a magnetic field; at least one gradient coil configured to linearly vary the magnetic field as a function of spatial location; at least one pulse-generating coil configured to generate and apply radio frequency (RF) pulses to the magnetic field in sequence to scan a portion of a subject; at least one shim gradient coil configured to perturb the magnetic field; and a control unit configured to: access an indication of at least one user-defined region that is both axially adjustable and laterally adjustable within a field-of-view, the field-of-view corresponding to a 2D image slice encompassing the at least one user-defined region, and operate the at least one gradient coil, the at least one pulse-generating coil, and the at least one shim gradient coil, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil.

In an implementation of the present disclosure, a method of magnetic resonance imaging (MRI) by way of an MRI system comprises: providing the MRI system, providing the MRI system comprising: providing a main magnet configured to generate a magnetic field; providing at least one gradient coil configured to linearly vary the magnetic field as a function of spatial location; providing at least one pulse-generating coil configured to generate and apply radio frequency (RF) pulses to the magnetic field in sequence to scan a portion of a subject; providing at least one shim gradient coil configured to perturb the magnetic field; and providing a control unit configured to: access an indication of at least one user-defined region that is both axially adjustable and laterally adjustable within a field-of-view, the field-of-view corresponding to a 2D image slice encompassing the at least one user-defined region, and operate the at least one gradient coil, the at least one pulse-generating coil, and the at least one shim gradient coil, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil; and operating the MRI system.

In an implementation of the present disclosure, a method of providing a magnetic resonance imaging (MRI) system comprises: providing a main magnet configured to generate a magnetic field; providing at least one gradient coil configured to linearly vary the magnetic field as a function of spatial location; providing at least one pulse-generating coil configured to generate and apply radio frequency (RF) pulses to the magnetic field in sequence to scan a portion of a subject; providing at least one shim gradient coil configured to perturb the magnetic field; and providing a control unit configured to: access an indication of at least one user-defined region that is both axially adjustable and laterally adjustable within a field-of-view, the field-of-view corresponding to a 2D image slice encompassing the at least one user-defined region, and operate the at least one gradient coil, the at least one pulse-generating coil, and the at least one shim gradient coil, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil.

The details of one or more aspects of the subject matter described in the present disclosure are set forth in the accompanying drawings and the below description. Other features, aspects, and advantages of the subject matter will become apparent from the description, the drawings, and the claims.

DETAILED DESCRIPTION

Figure 1A:
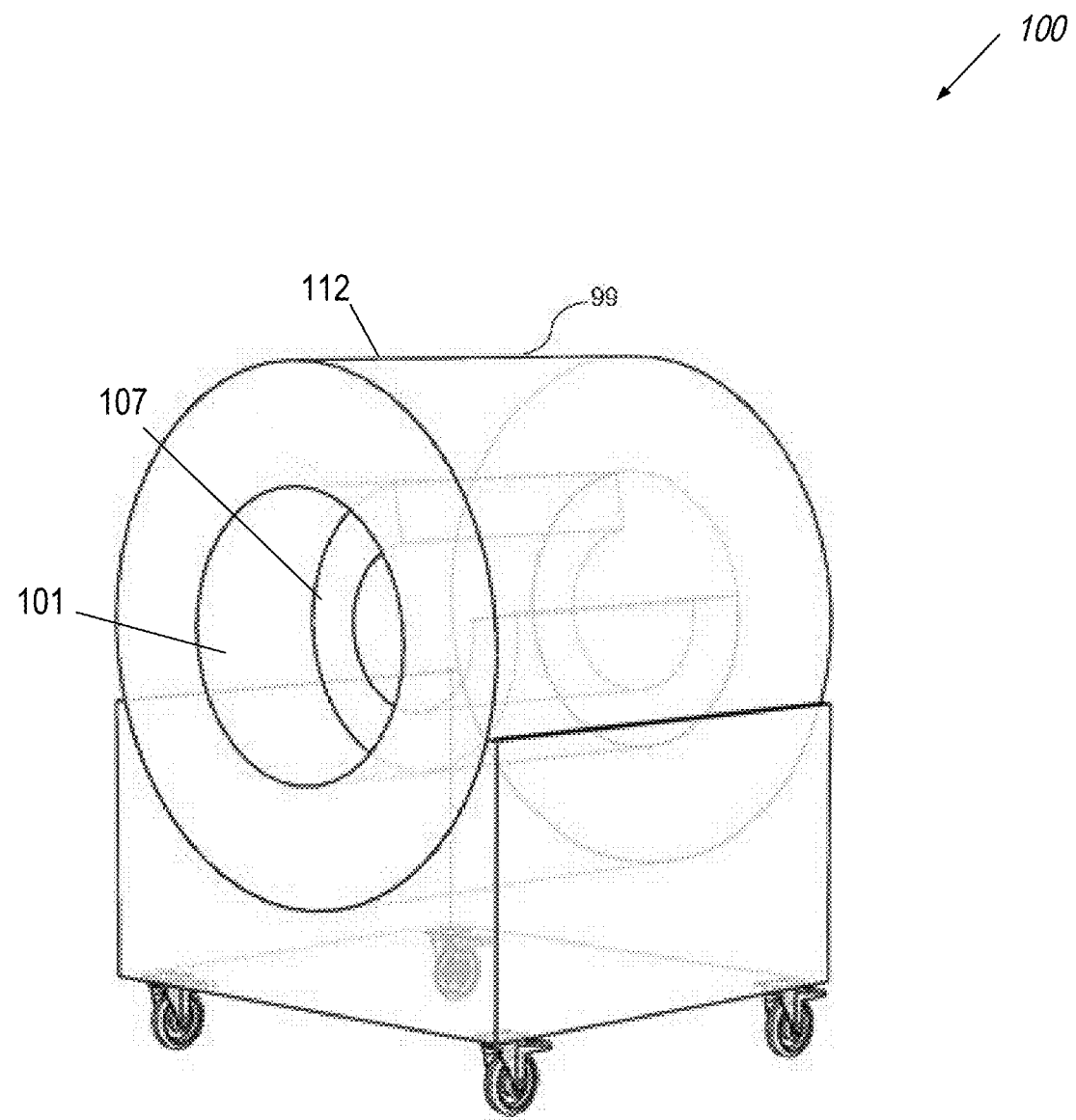
FIG. 1A is a diagram illustrating, in a perspective view, a magnetic resonance imaging (MRI) system, comprising a solenoid magnet, wherein a shimming coil is used to perturb a volume of uniform magnetic field inside the solenoid magnet, in accordance with an embodiment of the present disclosure.

Various embodiments and aspects of the disclosure will be below described with reference to details discussed. The following description and drawings are illustrative of the present disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

In general, one aspect of the subject matter described in the present disclosure involves a magnetic resonance imaging (MRI) system including: a housing having a bore in which at least a portion of a subject to be image is placed; a main magnet accommodated by the housing and configured to generate a volume of magnetic field within the bore, the volume of magnetic field having inhomogeneity below a defined threshold; one or more gradient coils configured to linearly vary the volume of magnetic field as a function of spatial location in the volume of magnetic field; one or more pulse-generating coils configured to generate and apply radio frequency (RF) pulses to the volume of magnetic field in sequence to scan the portion of the subject; one or more shim gradient coils configured to perturb a spatial distribution of the volume of magnetic field; and a control unit configured to: access an indication of at least one user-defined region to be imaged within the volume of magnetic field; and operate the gradient coils, pulse-generating coils, and shim gradient coils such that only the user-defined region within the volume of magnetic field is imaged.

Implementations may include one or more of the following features. For example, the system may operate the gradient coils, pulse-generating coils, and shim gradient coils such that only the user-defined region within the volume of magnetic field is imaged, the control unit is configured to operate the gradient coils, pulse-generating coils, and shim gradient coils such that a frequency response of the RF pulses has a coherent effect only within the user-defined region.

In some implementations, the system operates the gradient coils, pulse-generating coils, and shim gradient coils such that a frequency response of the RF pulses have a coherent effect only within the user-defined region, the control unit is configured to operate the gradient coils, pulse-generating coils, and shim gradient coils such that a resonant frequency of water falls outside of an RF bandwidth of the RF pulses in the regions of the volume of magnetic field outside of the user-defined region. In some implementations, the user-defined region is not centered on an isocenter of the volume of magnetic field. In some implementations, the user-defined region includes at least two regions that are unconnected regions within the volume of magnetic field.

In some implementations, the control unit is configured to access a second indication of a second user-defined region within the volume of magnetic field and operate the gradient coils, pulse-generating coils, and shim gradient coils such that only the second user-defined region within the volume of magnetic field is imaged, the second user-defined region having a different shape than the at least one user-defined region. In some implementations, the control unit is configured to access a second indication of a second user-defined region within the volume of magnetic field and operate the gradient coils, pulse-generating coils, and shim gradient coils such that only the second user-defined region within the volume of magnetic field is imaged, the second user-defined region having a different size than the at least one user-defined region.

Another aspect of the subject matter described in the present disclosure involves a method for operating a magnetic resonance imaging (MRI) system that includes a housing having a bore in which at least a portion of a subject to be image is placed, and a main magnet accommodated by the housing and configured to generate a volume of magnetic field within the bore having inhomogeneity below a defined threshold. The method may include: accessing an indication of at least one user-defined region to be imaged within the volume of magnetic field; operating one or more pulse-generating coils to generate and apply radio frequency (RF) pulses to the at least one user-defined region in sequence to scan the portion of the subject; operating one or more gradient coils to linearly vary the volume of magnetic field as a function of spatial location in the volume of magnetic field; and operating one or more shim gradient coils to perturb a spatial distribution of the at least one user-defined region.

In some implementations, operating the one or more pulse-generating coils to generate and apply radio frequency (RF) pulses includes operating the one or more pulse-generating coils such that a frequency response of the RF pulses has a coherent effect only within the user-defined region. In some implementations, operating one or more shim gradient coils to perturb a spatial distribution of the at least one user-defined region comprises operating the one or more shim gradient coils such that a resonant frequency of water falls outside of an RF bandwidth of the RF pulses in the regions of the volume of magnetic field outside of the user-defined region.

In some implementations, accessing an indication of at least one user-defined region to be imaged within the volume of magnetic field includes accessing an indication of at least one user-defined region that is not centered on an isocenter of the volume of magnetic field. In some implementations, accessing an indication of at least one user-defined region to be imaged within the volume of magnetic field includes accessing an indication of at least one user-defined region that includes at least two regions that are unconnected regions within the volume of magnetic field.

In some implementations, the method further includes: accessing a second indication of a second user-defined region within the volume of magnetic field; and operating the gradient coils, pulse-generating coils, and shim gradient coils such that only the second user-defined region within the volume of magnetic field is imaged, the second user-defined region having a different shape than the at least one user-defined region. In some implementations, the method further includes: accessing a second indication of a second user-defined region within the volume of magnetic field; and operating the gradient coils, pulse-generating coils, and shim gradient coils such that only the second user-defined region within the volume of magnetic field is imaged, the second user-defined region having a different size than the at least one user-defined region.

In MRI systems, a main magnet generates a highly uniform static magnetic field over a certain volume for imaging purposes. The region of uniformity, also referred to as the uniform magnetic field or main field homogeneity, is typically characterized by the maximum static field deviation over a certain spherical volume. The main magnet is designed to achieve a specific homogeneity, e.g., an inhomogeneity below the threshold, in order to generate an MR image for the imaging volume. When a subject, e.g., a human head, is inserted into the MRI scanner, tissue and any implantable devices in the subject may also affect the homogeneity of the imaging. The homogeneity can typically be improved through fine adjustment of active shimming coils such that the specific homogeneity is met.

In some reduced field-of-view MR imaging techniques, a baseline volume of a highly uniform static magnetic field is reduced in order to collect an MR image for a smaller region within the baseline volume. In this context, the field-of-view of an imaged region refers to the volume of highly uniform static magnetic field with a specific homogeneity. Thus, in reduced field-of-view MR imaging, the field-of-view refers to the smaller region within the baseline volume. The field-of-view used in magnetic resonance (MR) imaging often needs to be made large enough to avoid portions of an object of interest extending beyond the field-of-view to avoid signal wrap-around artifacts. However, this can also lead to significant amounts of time being used to encode spatial information across portions of anatomical objects that are not of interest. In addition, certain types of MR spatial encoding schemes can be sensitive to a variety of confounds such as field inhomogeneity, which can cause significant distortions and artifacts. In such instances, reduced field-of-view imaging can be used to restrict MR signals to smaller regions in order to generate spatial information from a reduced field to save time in encoding information specifically from a target region.

MR signals can be restricted using a shim gradient to perturb a volume of magnetic field that is used to generate an MR image such that the frequency response of the radiofrequency (RF) pulses used within an imaging sequence only have a coherent effect within the reduced field-of-view. As more particularly below described, the shim gradients can also be used to variably perturb the volume of magnetic field such that the reduced fields-of-view form different shapes and are positioned in different regions of the volume of magnetic field. According to selected embodiments, magnetic resonance imaging (MRI) systems can include an active coil, for example, integrated with gradient coils as one mechanical assembly to function as a location-specific static field shimming coil which, when activated, perturbs a spatial distribution of a volume of magnetic field over an MR imaging region such that the frequency response of radiofrequency (RF) pulses used in an imaging sequence have a coherent effect only within a user-defined region. Gradients applied to perturb the magnetic field using the shimming coils can be designed to create the user-defined regions of various shapes and sizes. As below described in more detail, some implementations may allow an operator, such as a clinician, to select a user-defined region to collect an image within an MR imaging region corresponding to a region of interest.

Figure 1B:
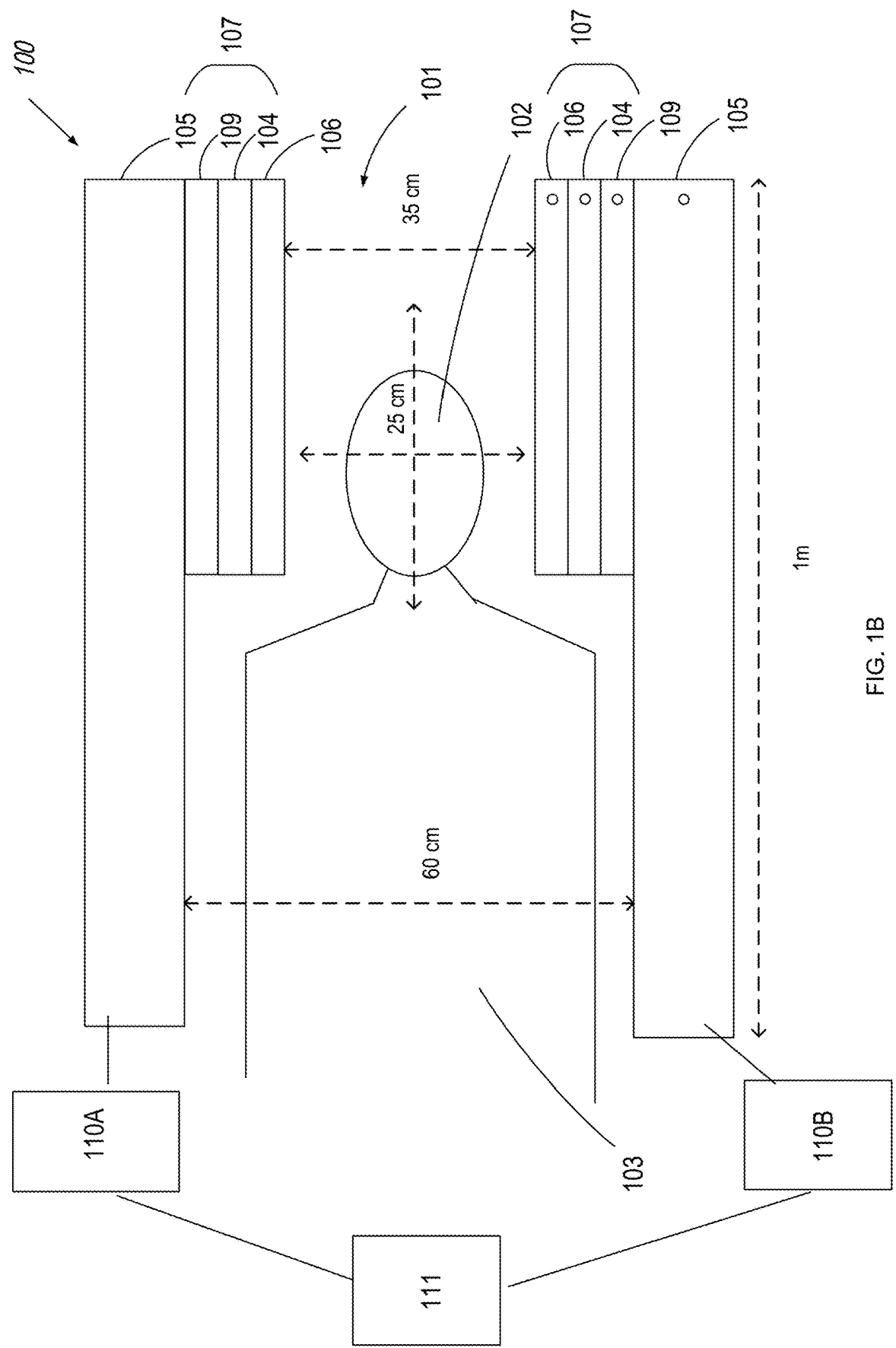
FIG. 1B is a diagram illustrating, in a cross-sectional view, a magnetic resonance imaging (MRI) system, wherein the shimming coil is used to perturb the volume of uniform magnetic field, in accordance with an embodiment of the present disclosure.

Referring to FIGS. 1A and 1B, together, these diagrams respectively illustrate, in a perspective view and a cross-sectional view, a magnetic resonance imaging (MRI) system 100 in which a solenoid magnet 105 is provided in a cylindrical shape housing 99 with an inner bore 101, in accordance with embodiments of the present disclosure. Coil assembly 107, including a pulse-generating coil 106 and a gradient coil 104, is provided within solenoid magnet 105. Coil assembly 107 may generally be shaped as an annular structure and housed within the inner bore of solenoid magnet 105. In some implementations, annular coil assembly 107 only includes gradient coil 104. Gradient coil 104 generally provides field gradients in more than one direction, such as, for example, all three orthogonal spatial directions. Thus, gradient coil 104 may refer to three sets of coils, each configured to generate field fluctuations in a respective direction for the main field in the inner bore of the solenoid magnet 105. Such field fluctuations may cause magnetizations from various spatial locations to experience precessions at different frequencies, enabling encoding of spatial information of the magnetizations through RF excitation pulses. The pulse-generating coil 106 can be configured to generate and apply RF pulses to the volume of magnetic field in sequence to scan a portion of patient 103, e.g., the head region 102.

Still referring to FIGS. 1A and 1B, together, for context, the main magnet of the MRI system 100 generates a highly-uniform static magnetic field over a certain volume for imaging purposes. Although small static field variations on the order of parts per million (ppm) can be tolerated, it is not possible to generate MR data in locations where the main field deviates too greatly, e.g., over hundreds of parts per million (ppm) over a 20 centimeter diameter spherical volume. For example, 40 ppm over a 25-cm diameter spherical volume (DSV) can represent a maximum $\Delta B0 = B0_{max} - B0_{min} = 20$ µT field deviation at a static field of $B0 = 0.5$ T.

Still referring to FIGS. 1A and 1B, together, the main magnet is designed to achieve a specific homogeneity (that is, the main magnet is designed to have an inhomogeneity below the threshold). However, the actual homogeneity at the installation site may be affected by material in or around the MRI scanner. At the time of installation, passive and/or active shim coils, e.g., the shim gradient coils 109, may be applied to improve the homogeneity so that it meets the specific homogeneity the main magnet is designed to achieve before subjects are placed in the inner bore 101. When a human head 102 of a subject, e.g., a patient 103, is inserted into the MRI scanner, the tissue and any implantable devices in the subject may also affect the homogeneity of the imaging volume and the homogeneity is again typically improved through fine adjustment of active shim coils, such as for example, through shim gradient coils 109, so that the specific homogeneity is met.

Still referring to FIGS. 1A and 1B, together, to quantify main field homogeneity, some implementations may measure, for example, the spectral width of the free induction decay (FID) signal from the region of interest. In this measure, field homogeneity may hinge on the spectral width of the FID signal to be below a defined threshold. More specifically, if the spectral width of the FID signal is satisfactorily narrow for the desired imaging application, for example, below a defined spectral width value, shimming may be deemed satisfactory. Otherwise, additional shimming may be performed to further reduce the spectral width of the FID signal. In these implementations, annular coil assembly may not include pulse-generating coil 106 or any receiver coil. For these implementations, radio-frequency (RF) excitation pulses are, for example, transmitted by local coils, e.g., pulse-generating coils, for imaging the head region 102 of patient 103. In one instance, a head coil in a birdcage configuration is used for both transmitting RF excitation pulses and receiving MR signals for imaging the subject. In another instance, the pulse-generating coil 106 is a surface coil that is used for transmitting an RF excitation pulse into the subject and a phased array coil configuration is used for receiving MR signals in response.

Still referring to FIGS. 1A and 1B, together, the shim gradient coils 109 are housed within the cylindrical walls of solenoid magnet 105. Shim gradient coils 109 are powered by a group of power amplifiers 110A and 110B. In some cases, the power amplifiers 110A and 110B are housed in a control room and are connected to shim gradient coils 109 to provide shimming of the magnetic field within inner bore 101. In driving shim gradient coils 109, power amplifiers 110A and 110B are controlled by a control unit 111. The driving current for shim gradient coils 109 may be in the range of hundreds of milliamperes and generally may not exceed 1 ampere. Further, shim gradient coils 109 may not require active cooling using circulating coolant. In these implementations, an array of shimming coils can be used to provide adjustment to the field strength within the inner bore 101 such that the magnetic field within the inner bore 101 becomes more homogenous. The shimming coils 109 produce spatial magnetic field perturbations which are in well-defined polynomial spatial patterns, e.g., xy, $x^2$, $y^2$. In some implementations, the shimming coils 109 can be dynamically configured to produce arbitrary spatially varying patterns in the magnetic field.

Still referring to FIGS. 1A and 1B, together, the control unit 111 generally includes one or more processors as well as programming logic to configure the power amplifiers 110A and 110B to adjust the operation of the shim gradient coils 109. As described more specifically below, the control unit 111 can be configured to access an indication of a user-defined region to be imaged within the volume of magnetic field, and operate the gradient coil 104, the pulse-generating coil 106, and the shim gradient coil 109 such that only the user-defined region within the volume of magnetic field is imaged. In some implementations, the control unit 111 is configured to operate the gradient coil 104, the pulse-generating coil 106, and the shim gradient coil 109 such that a frequency response of the RF pulses has a coherent effect only within the user-defined region.

Figure 2A:
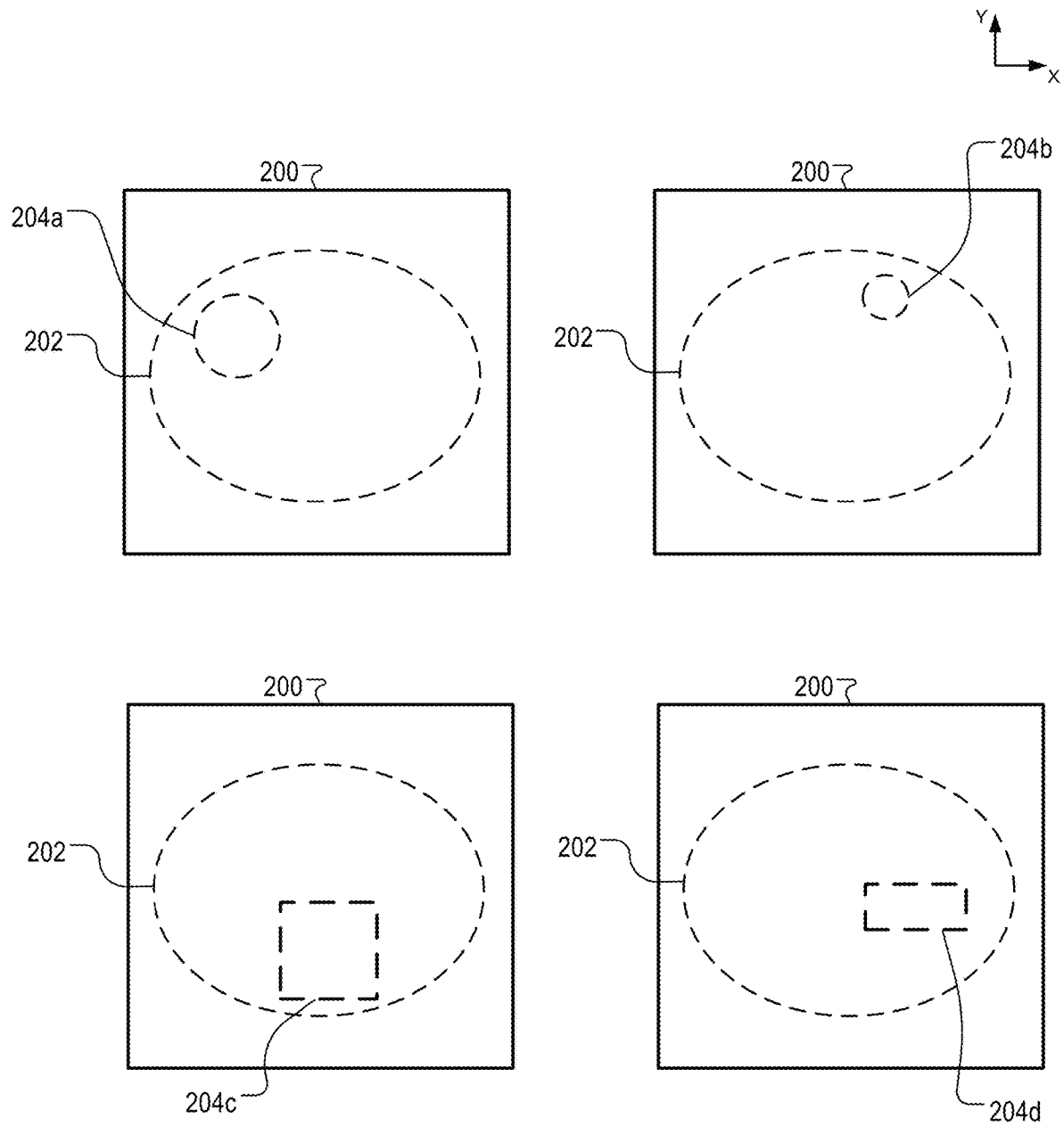
FIG. 2A is a diagram illustrating adjustable imaging regions within a magnetic resonance (MR) image, in accordance with an embodiment of the present disclosure.
Figure 2B:
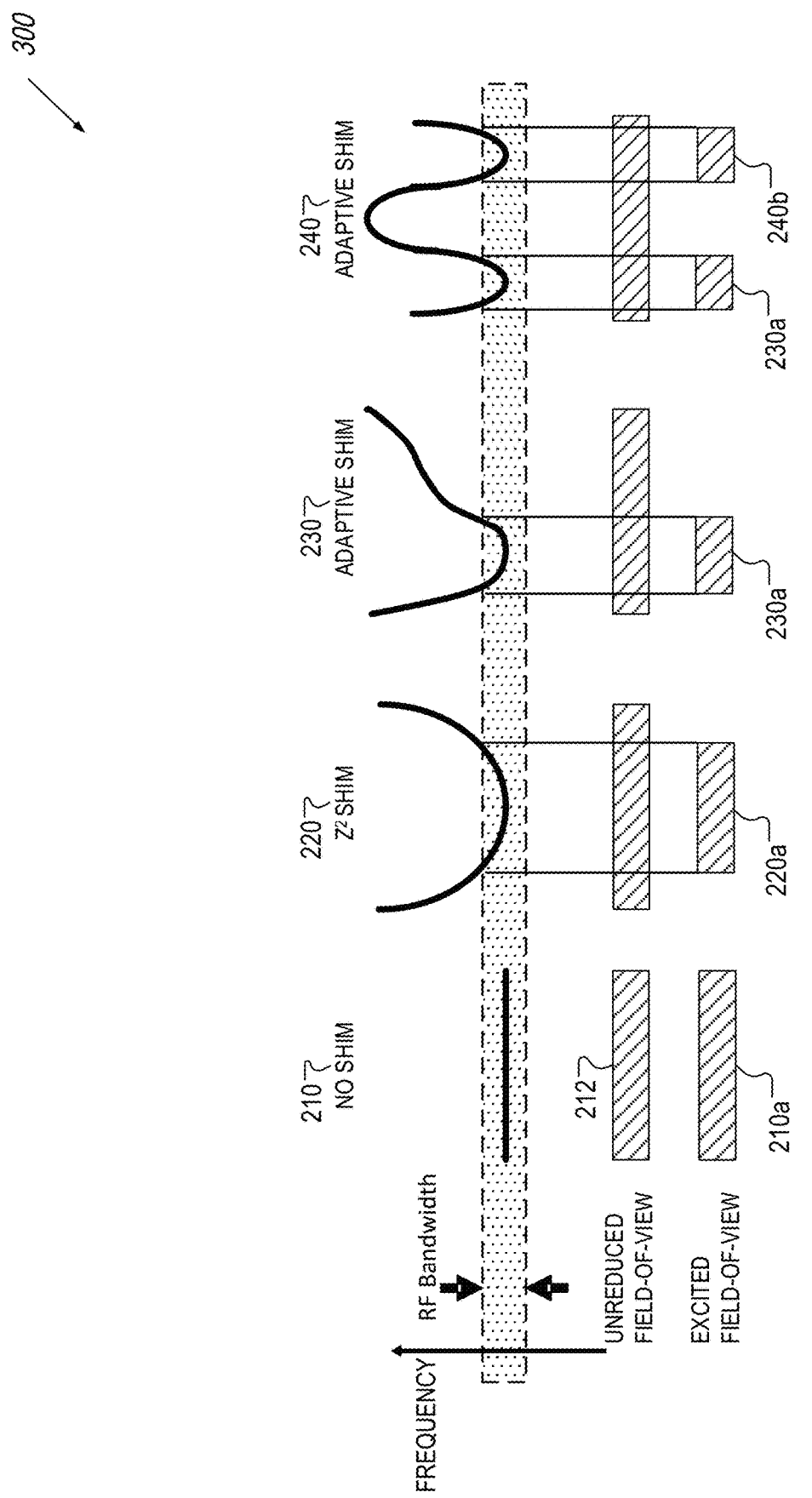
FIG. 2B is a diagram illustrating shimming coil gradients used to perturb a spatial distribution of a volume of magnetic field over an MR imaging region, in accordance with an embodiment of the present disclosure.

Referring to FIGS. 2A and 2B, together, these diagrams illustrate the user-defined region within the volume of magnetic field that is imaged can be variably configured based on the shim gradient patterns, in accordance with embodiments of the present disclosure. For example, in some instances, the user-defined region includes at least two regions that are unconnected regions within the volume of magnetic field. In other instances, the user-defined region can be configured to have different shapes and different sizes.

Still referring to FIGS. 2A and 2B, together, in more detail, the control unit 111 configures the shim gradient coils 109 to generate different shimming gradients that variably perturb a spatial distribution of the volume of magnetic field applied over the inner bore 101. In some instances, the control unit 111 is housed in a control room separate from the solenoid magnet 105 of the MRI system 100. In some implementations, the control unit 111 includes a user interface that allows an operator such as a clinician or technician to adjust the shimming gradient applied by the shim gradient coils 109 to the inner bore 101. For example, in such implementations, the control unit 111 presents the operator with a set of different gradient patterns that are selectable by the operator. In response to receiving user selection of a gradient pattern on the user interface, the control unit 111 then transmits control signals to the power amplifiers 110A to 110B to adjust the operation of the shim gradient coils 109 to generate the selected gradient pattern.

Still referring to FIGS. 2A and 2B, together, the user interface on the control unit 111 can additionally be used to specify adaptive gradient patterns that are customized for a particular region within the volume of static magnetic field used to generate an MR image. For example, as depicted in FIG. 2A, the custom gradient patterns can be used to adjust the field-of-view of the MRI image captured of the patient 103. In these examples, the user interface of the control unit 111 displays a custom gradient pattern generator that allows the operator to adjust the shape, magnitude, and other features of the gradient pattern. The user interface also displays a predicted field-of-view of the MRI image resulting from the custom gradient pattern. The predicted field-of-view of the MRI can be adjusted in real-time with changes made by the operator on the custom gradient pattern generator such that the user interface allows the operator to configure the field-of-view to specific regions of interest. For instance, the predicted field-of-view may be superimposed over a baseline MR image to spatially coordinate the predicted field-of-view to anatomical features of interest.

Referring back to FIG. 2A, this diagram illustrates examples of adjustable imaging regions 204a-204d of a region 202 within an MRI field-of-view 200. The MRI system 100 initially generates a highly uniform static magnetic field over the region 202 for imaging purposes within the field-of-view 200 of the MRI system 100. The generated magnetic field can then be perturbed using the shim gradient coils 109 in order to adjust the spatial distribution of the magnetic field over the region 202. In this regard, different shimming coil patterns may be used to generate various user-defined imaging regions such as the adjustable imaging regions 204a-204d.

Still referring back to FIG. 2A, adjustable imaging regions 204a-204d represent examples of customizable regions that are imaged within a region 202. As depicted, the adjustable imaging regions 204a-204d may vary in size and shape based on the specific perturbation of the spatial distribution of magnetic field over the region 202 along the respective horizontal and vertical axis of the field-of-view 200, e.g., x-axis and y-axis. Although the adjustable imaging regions 204a-204d are depicted as symmetrical shapes, e.g., circles, rectangles, squares, etc., in FIG. 2A, in some instances, perturbation of the spatial distribution of magnetic field over the region 202 can also be used to generate arbitrary shapes and sizes. In addition, the perturbation can also be applied such that multiple imaging regions within the region 202 can be used for localized imaging of specific structures within the MRI field-of-view 200.

Still referring back to FIG. 2A, in changing the spatial distribution of the magnetic field, the applied shim gradient also changes the spatial distribution of the resonant frequency of water. Thus, the shim gradient can be applied to shift the resonant frequency of water outside the bandwidth of the RF pulse in certain regions over the region 202 such that water in these regions are unaffected by the RF pulse and do not contribute to the resultant MR image. In contrast, the resonant frequency of water included within the adjustable imaging regions 204a-204d are within the bandwidth of the RF pulse such that the resultant MR image only includes spatial information from the water included within the adjustable imaging regions 204a-204d.

Still referring back to FIG. 2A, the perturbation of the spatial distribution of the static magnetic field over the region 202 causes the frequency response of the RF pulses used in an imaging sequence to have a coherent effect only within the adjustable imaging regions 204a-204d. For example, during an imaging sequence over the region 202, a shim gradient may also be applied over the region 202 using the shim gradient coils 109 to create a spatially varying effect to the distribution of magnetic field over the volume of magnetic field. In some implementations, the shim gradient may be applied at the same time as a standard slice-selective excitation during an MR imaging sequence. In other implementations, the shim gradient may be applied during an MR imaging refocusing pulse.

Referring back to FIG. 2B, different shim gradient patterns can be used to excite specific regions of an unreduced field-of-view 212 during an MR image sequence. For instance, in 210, because there is no shim gradient applied to the region 202, the resonant frequency of all of the water within the unreduced field-of-view 212 falls within the bandwidth of the RF pulse, resulting in an excited field-of-view 210a that is includes the entire unreduced field-of-view 212. In contrast, when using a shim gradient 220, the resonant frequency of water falls outside the bandwidth near the edges of the unreduced field-of-view 212, which results in an excited field-of-view 220a that only includes the center portion of the unreduced field-of-view 212.

Still referring back to FIG. 2B, the shimming coils 109 produce spatial magnetic field perturbations which are in well-defined polynomial spatial patterns, e.g., xy, $x^2$, $y^2$. In some implementations, the shimming coils 109 can be dynamically configured to produce arbitrary spatially varying patterns in the magnetic field using adaptive gradients 230 and 240. Adaptive gradients 230 and 240 can be used to apply specific changes to the spatial distribution of the resonant frequency of water such that the excited regions 230a and 240b are not centered on the isocenter of the magnetic field over the field-of-view 212. For example, the adaptive gradient 230 causes only a decrease in resonant frequency near the left portion of the field-of-view 212 such an excited field-of-view 230a only includes a left portion of the field-of-view 212 but not the right portion of the field-of-view 212 that includes water with a resonant frequency above the RF bandwidth. In another example, the adaptive gradient 240 causes a decrease in resonant frequency in multiple regions of the field-of-view 212 such that multiple excited field-of-views 240a and 240b are created within the field-of-view 212. In this example, the adaptive gradient 240 causes a sinusoidal change in resonant frequency along the horizontal axis of the field-of-view 212.

Figure 3:
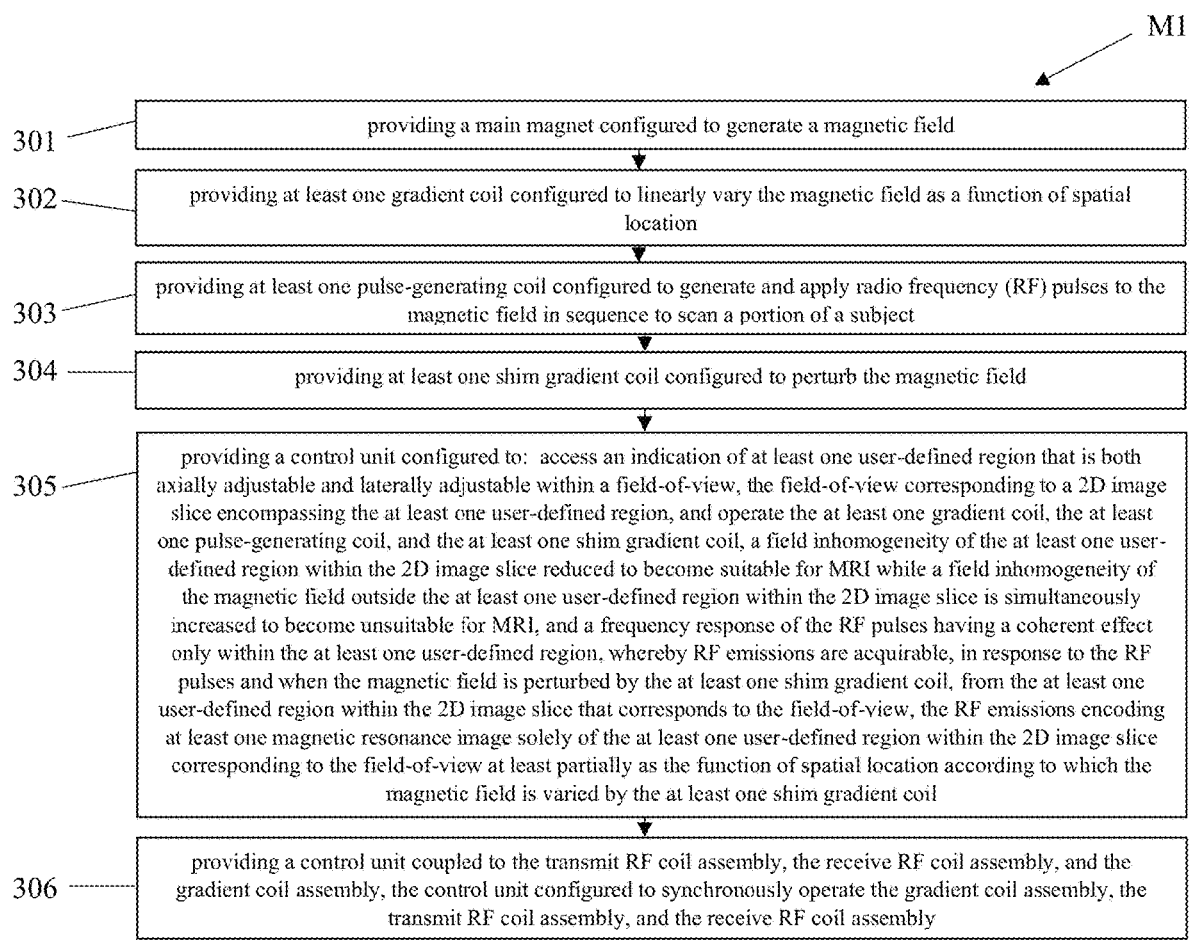
FIG. 3 is a flow diagram illustrating a method of providing an MRI system, in accordance with an embodiment of the present disclosure.
Figure 4:
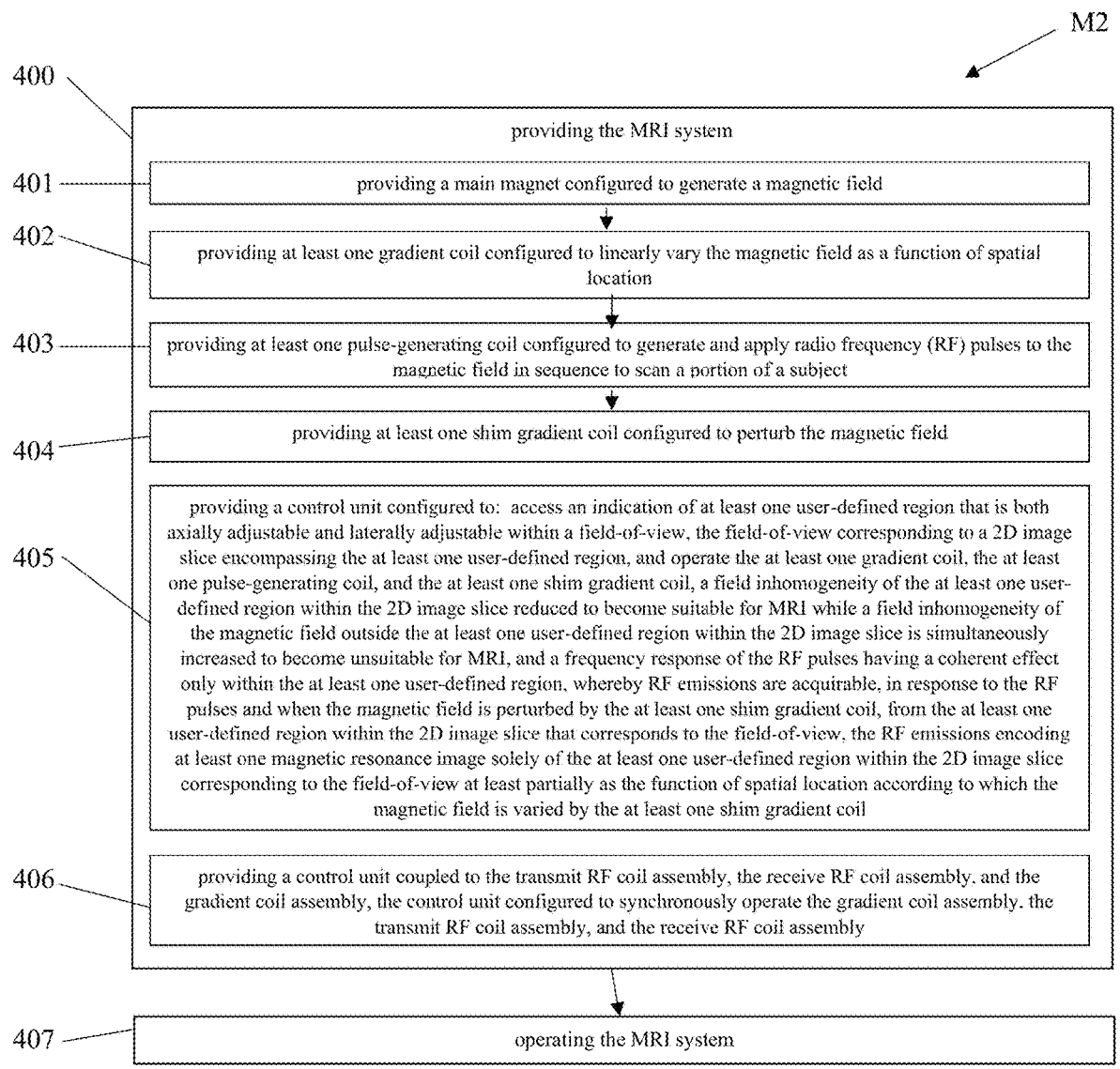
FIG. 4 is a flow diagram illustrating a method of magnetic resonance imaging by way of an MRI system, in accordance with an embodiment of the present disclosure.

Referring back to FIGS. 1A-2B and referring ahead to FIGS. 3 and 4, in an embodiment of the present disclosure, a magnetic resonance imaging (MRI) system 100 comprises: a main magnet, e.g., the solenoid magnet 105, configured to generate a magnetic field; at least one gradient coil, e.g., the gradient coil 104, configured to linearly vary the magnetic field as a function of spatial location; at least one pulse-generating coil, e.g., the pulse-generating coil 106, configured to generate and apply radio frequency (RF) pulses to the magnetic field in sequence to scan a portion, e.g., the head 102, of a subject, e.g., the patient 103; at least one shim gradient coil, e.g., the shim gradient coil 109, configured to perturb the magnetic field; and a control unit 111 configured to: access an indication of at least one user-defined region that is both axially adjustable and laterally adjustable within a field-of-view, the field-of-view corresponding to a 2D image slice encompassing the at least one user-defined region, and operate the at least one gradient coil, e.g., the gradient coil 104, the at least one pulse-generating coil, e.g., the pulse-generating coil 106, and the at least one shim gradient coil, e.g., the shim gradient coil 109, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, e.g., the shim gradient coil 109, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil e.g., the shim gradient coil 109.

Still referring back to FIGS. 1A-2B and referring ahead to FIGS. 3 and 4, the system 100 further comprising a housing 99 configured to accommodate the main magnet, e.g., the solenoid magnet 105, and having a bore, e.g., the inner bore 101, configured to accommodate at least the portion, e.g., the head 102, of the subject, e.g., the patient 103. In the system 100, at least one of: the control unit 111 is further configured to operate the at least one gradient coil, e.g., the gradient coil 104, the at least one pulse-generating coil, e.g., the pulse-generating coil 106, and the at least one shim gradient coil, e.g., the shim gradient coil 109, wherein a resonant frequency of water falls outside of an RF bandwidth of the RF pulses in the magnetic field outside the at least one user-defined region; the user-defined region is disposed away from an isocenter of the magnetic field; the at least one user-defined region comprises a plurality of unconnected regions within the magnetic field; the control unit 111 is further configured to access a new indication of a new user-defined region within the magnetic field; and the control unit 111 is configured to operate the at least one gradient coil, e.g., the gradient coil 104, the at least one pulse-generating coil, e.g., the pulse-generating coil 106, and the at least one shim gradient coil, e.g., the shim gradient coil 109, to obtain at least one magnetic resonance image of the new user-defined region within the magnetic field, the new user-defined region comprising at least one of a different shape than that of the at least one user-defined region and a different size than that of the at least one user-defined region.

Referring to FIG. 3, this flow diagram illustrates a method M1 of providing an MRI system 100, in accordance with an embodiment of the present disclosure. The method M1 comprises: providing a main magnet, e.g., the solenoid magnet 105, configured to generate a magnetic field, as indicated by block 301; providing at least one gradient coil, e.g., the gradient coil 104, configured to linearly vary the magnetic field as a function of spatial location, as indicated by block 302; providing at least one pulse-generating coil, e.g., the pulse-generating coil 106, configured to generate and apply radio frequency (RF) pulses to the magnetic field in sequence to scan a portion of a subject, as indicated by block 303; providing at least one shim gradient coil, e.g., the shim gradient coil 109, configured to perturb the magnetic field, as indicated by block 304; and providing a control unit 111 configured to: access an indication of at least one user-defined region that is both axially adjustable and laterally adjustable within a field-of-view, the field-of-view corresponding to a 2D image slice encompassing the at least one user-defined region, and operate the at least one gradient coil, e.g., the gradient coil 104, the at least one pulse-generating coil, e.g., the pulse-generating coil 106, and the at least one shim gradient coil, e.g., the shim gradient coil 109, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, e.g., the shim gradient coil 109, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil, e.g., the shim gradient coil 109, as indicated by block 305.

Still referring to FIG. 3, the method M1 further comprises providing a housing 99 configured to accommodate the main magnet, e.g., the gradient coil 104, and having a bore, e.g., the inner bore 101, configured to accommodate at least the portion, e.g., the head 102, of the subject, e.g., the patient 103, as indicated by block 306. In the method M1, at least one of: providing the control unit 111, as indicated by block 305, further comprises configuring the control unit 111 to operate the at least one gradient coil, e.g., the gradient coil 104, the at least one pulse-generating coil, e.g., the pulse-generating coil 106, and the at least one shim gradient coil, e.g., the shim gradient coil 109, wherein a resonant frequency of water falls outside of an RF bandwidth of the RF pulses in the magnetic field outside the at least one user-defined region; providing the control unit 111, as indicated by block 305, comprises configuring the control unit 111 to access the indication of the at least one user-defined region that is disposed away from an isocenter of the magnetic field; providing the control unit 111 comprises further configuring the control unit 111 to access a new indication of a new user-defined region within the magnetic field; and providing the control unit 111, as indicated by block 305, comprises further configuring the control unit 111 to operate the at least one gradient coil, e.g., the gradient coil 104, the at least one pulse-generating coil, e.g., the pulse-generating coil 106, and the at least one shim gradient coil, e.g., the shim gradient coil 109, to obtain at least one magnetic resonance image of the new user-defined region within the magnetic field, the new user-defined region comprising at least one of a different shape than that of the at least one user-defined region and a different size than that of the at least one user-defined region.

Referring to FIG. 4, this flow diagram illustrates a method M2 of magnetic resonance imaging by way of an MRI system 100, in accordance with an embodiment of the present disclosure. The method M2 comprises: providing the MRI system 100, as indicated by block 400, providing the MRI system 100 comprising: providing a main magnet, e.g., the solenoid magnet 105, configured to generate a magnetic field, as indicated by block 401; providing at least one gradient coil, e.g., the gradient coil 104, configured to linearly vary the magnetic field as a function of spatial location, as indicated by block 402; providing at least one pulse-generating coil, e.g., the pulse-generating coil 106, configured to generate and apply radio frequency (RF) pulses to the magnetic field in sequence to scan a portion of a subject, as indicated by block 403; providing at least one shim gradient coil, e.g., the shim gradient coil 109, configured to perturb the magnetic field, as indicated by block 404; and providing a control unit 111 configured to: access an indication of at least one user-defined region that is both axially adjustable and laterally adjustable within a field-of-view, the field-of-view corresponding to a 2D image slice encompassing the at least one user-defined region, and operate the at least one gradient coil, e.g., the gradient coil 104, the at least one pulse-generating coil, e.g., the pulse-generating coil 106, and the at least one shim gradient coil, e.g., the shim gradient coil 109, a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, e.g., the shim gradient coil 109, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil, e.g., the shim gradient coil 109, as indicated by block 405; and operating the MRI system, as indicated by block 407.

Still referring to FIG. 4, the method M2 further comprises providing a housing 99 configured to accommodate the main magnet, e.g., the gradient coil 104, and having a bore, e.g., the inner bore 101, configured to accommodate at least the portion, e.g., the head 102, of the subject, e.g., the patient 103, as indicated by block 406. In the method M1, at least one of: providing the control unit 111, as indicated by block 405, further comprises configuring the control unit 111 to operate the at least one gradient coil, e.g., the gradient coil 104, the at least one pulse-generating coil, e.g., the pulse-generating coil 106, and the at least one shim gradient coil, e.g., the shim gradient coil 109, wherein a resonant frequency of water falls outside of an RF bandwidth of the RF pulses in the magnetic field outside the at least one user-defined region; providing the control unit 111, as indicated by block 405, comprises configuring the control unit 111 to access the indication of the at least one user-defined region that is disposed away from an isocenter of the magnetic field; providing the control unit 111 comprises further configuring the control unit 111 to access a new indication of a new user-defined region within the magnetic field; and providing the control unit 111, as indicated by block 405, comprises further configuring the control unit 111 to operate the at least one gradient coil, e.g., the gradient coil 104, the at least one pulse-generating coil, e.g., the pulse-generating coil 106, and the at least one shim gradient coil, e.g., the shim gradient coil 109, to obtain at least one magnetic resonance image of the new user-defined region within the magnetic field, the new user-defined region comprising at least one of a different shape than that of the at least one user-defined region and a different size than that of the at least one user-defined region.

The embodiments provided herein may be adapted for intraoperative MRI, and MRI systems for use in an emergency room setting. Such MRI systems may include a smaller and more compact bore size magnet compared to the magnets from conventional whole body scanners.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed:

1. A magnetic resonance imaging (MRI) system, comprising:
   a main magnet configured to generate a magnetic field;
   at least one gradient coil configured to linearly vary the magnetic field as a function of spatial location;
   at least one pulse-generating coil configured to generate and apply radio frequency (RF) pulses to the magnetic field in sequence to scan a portion of a subject;
   at least one shim gradient coil configured to perturb the magnetic field; and
   a control unit configured to:
   access an indication of at least one user-defined region that is both axially adjustable and laterally adjustable within a field-of-view, the field-of-view corresponding to a 2D image slice encompassing the at least one user-defined region, and
   operate the at least one gradient coil, the at least one pulse-generating coil, and the at least one shim gradient coil, such that a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil.

2. The system of claim 1, further comprising a housing configured to accommodate the main magnet and having a bore configured to accommodate at least the portion of the subject.

3. The system of claim 1, wherein the control unit is further configured to operate the at least one gradient coil, the at least one pulse-generating coil, and the at least one shim gradient coil, wherein a resonant frequency of water falls outside of an RF bandwidth of the RF pulses in the magnetic field outside the at least one user-defined region.

4. The system of claim 1, wherein the user-defined region is disposed away from an isocenter of the magnetic field.

5. The system of claim 1, wherein the at least one user-defined region comprises a plurality of unconnected regions within the magnetic field.

6. The system of claim 1, wherein the control unit is further configured to access a new indication of a new user-defined region within the magnetic field.

7. The system of claim 6, wherein the control unit is configured to operate the at least one gradient coil, the at least one pulse-generating coil, and the at least one shim gradient coil to obtain at least one magnetic resonance image of the new user-defined region within the magnetic field, the new user-defined region comprising at least one of a different shape than that of the at least one user-defined region and a different size than that of the at least one user-defined region.

8. A method of magnetic resonance imaging (MRI) by way of an MRI system, the method comprising:
   providing the MRI system, providing the MRI system comprising:
   providing a main magnet configured to generate a magnetic field;
   providing at least one gradient coil configured to linearly vary the magnetic field as a function of spatial location;
   providing at least one pulse-generating coil configured to generate and apply radio frequency (RF) pulses to the magnetic field in sequence to scan a portion of a subject;
   providing at least one shim gradient coil configured to perturb the magnetic field; and
   providing a control unit configured to:
   access an indication of at least one user-defined region that is both axially adjustable and laterally adjustable within a field-of-view, the field-of-view corresponding to a 2D image slice encompassing the at least one user-defined region, and
   operate the at least one gradient coil, the at least one pulse-generating coil, and the at least one shim gradient coil, such that a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil; and operating the MRI system.

9. The method of claim 8, wherein providing the MRI system further comprises providing a housing configured to accommodate the main magnet and having a bore configured to accommodate at least the portion of the subject.

10. The method of claim 8, wherein providing the control unit further comprises configuring the control unit to operate the at least one gradient coil, the at least one pulse-generating coil, and the at least one shim gradient coil, wherein a resonant frequency of water falls outside of an RF bandwidth of the RF pulses in the magnetic field outside the at least one user-defined region.

11. The method of claim 8, wherein providing the control unit comprises configuring the control unit to access the indication of the at least one user-defined region that is disposed away from an isocenter of the magnetic field.

12. The method of claim 8, wherein providing the control unit comprises configuring the control unit to access the indication of the at least one user-defined region comprising a plurality of unconnected regions within the magnetic field.

13. The method of claim 8, wherein providing the control unit comprises further configuring the control unit to access a new indication of a new user-defined region within the magnetic field.

14. The method of claim 13, wherein providing the control unit comprises further configuring the control unit to operate the at least one gradient coil, the at least one pulse-generating coil, and the at least one shim gradient coil to obtain at least one magnetic resonance image of the new user-defined region within the magnetic field, the new user-defined region comprising at least one of a different shape than that of the at least one user-defined region and a different size than that of the at least one user-defined region.

15. A method of providing a magnetic resonance imaging (MRI) system, the method comprising:

providing a main magnet configured to generate a magnetic field;

providing at least one gradient coil configured to linearly vary the magnetic field as a function of spatial location;

providing at least one pulse-generating coil configured to generate and apply radio frequency (RF) pulses to the magnetic field in sequence to scan a portion of a subject;

providing at least one shim gradient coil configured to perturb the magnetic field; and providing a control unit configured to:

access an indication of at least one user-defined region that is both axially adjustable and laterally adjustable within a field-of-view, the field-of-view corresponding to a 2D image slice encompassing the at least one user-defined region, and operate the at least one gradient coil, the at least one pulse-generating coil, and the at least one shim gradient coil, such that a field inhomogeneity of the at least one user-defined region within the 2D image slice reduced to become suitable for MRI while a field inhomogeneity of the magnetic field outside the at least one user-defined region within the 2D image slice is simultaneously increased to become unsuitable for MRI, and a frequency response of the RF pulses having a coherent effect only within the at least one user-defined region, whereby RF emissions are acquirable, in response to the RF pulses and when the magnetic field is perturbed by the at least one shim gradient coil, from the at least one user-defined region within the 2D image slice that corresponds to the field-of-view, the RF emissions encoding at least one magnetic resonance image solely of the at least one user-defined region within the 2D image slice corresponding to the field-of-view at least partially as the function of spatial location according to which the magnetic field is varied by the at least one shim gradient coil.

16. The method of claim 15, wherein providing the MRI system further comprises providing a housing configured to accommodate the main magnet and having a bore configured to accommodate at least the portion of the subject.

17. The method of claim 15, wherein providing the control unit further comprises configuring the control unit to operate the at least one gradient coil, the at least one pulse-generating coil, and the at least one shim gradient coil, wherein a resonant frequency of water falls outside of an RF bandwidth of the RF pulses in the magnetic field outside the at least one user-defined region.

18. The method of claim 15, wherein providing the control unit comprises configuring the control unit to access the indication of the at least one user-defined region that is disposed away from an isocenter of the magnetic field.

19. The method of claim 15, wherein providing the control unit comprises further configuring the control unit to access a new indication of a new user-defined region within the magnetic field.

20. The method of claim 19, wherein providing the control unit comprises further configuring the control unit to operate the at least one gradient coil, the at least one pulse-generating coil, and the at least one shim gradient coil to obtain at least one magnetic resonance image of the new user-defined region within the magnetic field, the new user-defined region comprising at least one of a different shape than that of the at least one user-defined region and a different size than that of the at least one user-defined region.

* * * * *